United States Patent [19]

Loken et al.

[11] Patent Number: 5,047,321

[45] Date of Patent: Sep. 10, 1991

[54] METHOD FOR ANALYSIS OF CELLULAR COMPONENTS OF A FLUID

[75] Inventors: Michael R. Loken, Los Altos; Leon W. M. M. Terstappen, Palo Alto, both of Calif.

[73] Assignee: Becton Dickinson & Co., Franklin Lakes, N.J.

[21] Appl. No.: 207,099

[22] Filed: Jun. 15, 1988

[51] Int. Cl.$^5$ .................... C12Q 1/68; G01N 33/577
[52] U.S. Cl. .......................................... 435/6; 435/4; 435/7.21; 435/7.24; 435/34; 435/973; 436/63; 436/94; 436/164; 436/172; 436/519; 436/548; 436/800; 436/805; 935/110
[58] Field of Search .................. 435/4, 6, 7, 808, 810, 435/7.21, 7.24, 7.25, 973, 34; 436/501, 503, 63, 74, 172, 800, 824, 808, 94, 519, 164, 548, 805; 424/85.8; 935/110

[56] References Cited

U.S. PATENT DOCUMENTS

| | | | |
|---|---|---|---|
| 3,826,364 | 7/1974 | Bonner et al. | 209/3 |
| 4,284,412 | 8/1981 | Hansen et al. | 23/230 |
| 4,520,110 | 5/1985 | Stryer et al. | 436/501 |
| 4,544,546 | 10/1985 | Wang et al. | 424/7.1 |
| 4,661,913 | 4/1987 | Wu et al. | 364/500 |
| 4,727,020 | 2/1988 | Recktenwald | 436/6 |
| 4,883,867 | 11/9189 | Lee et al. | 436/10 |

OTHER PUBLICATIONS

Becton Dickinson Immunocytometry Systems, Source Book Section 4.24.
Coulter, Proc. Nat. Electronics Conf., 12:1034 (1956).
Breakell et al., Blood Cells, 11:257 (1985).
Herzenberg et al., Sci. Am., 234:108 (1976).
Shapiro et al., J. Histochem & Cytochem., 24:396 (1976).
Shapiro et al., J. Histochem & Cytochem., 25:836 (1977).

*Primary Examiner*—David A. Saunders
*Attorney, Agent, or Firm*—Robert M. Hallenbeck

[57] ABSTRACT

A method for multi-parameter analysis of cells in a body fluid sample is described which makes use of a plurality of fluorescence measurements, comprising at least two nucleic acid dyes and at least one fluorescently labelled cell surface marker, and a plurality of light scattering measurements. A kit containing the nucleic acid dyes and cell surface marker also is described.

16 Claims, 6 Drawing Sheets

METHOD FOR ANALYSIS OF CELLULAR COMPONENTS OF A FLUID

FIELD OF INVENTION

This invention relates to the multi-parameter analysis of cellular components in a body fluid, and more particularly, it relates to the discrimination and quantification of the cellular components of blood or bone marrow aspirates through analysis of five parameters by flow cytometry.

BACKGROUND OF THE INVENTION

Two of the most important measures of the hematologic status of an individual are the whole blood count and leukocyte differential. Whole blood counts and leukocyte differentials involve the discrimination and then counting of the various cellular components of blood. The various components of blood that may appear in any one sample include red blood cells (RBC), platelets and nucleated cells. In the latter category, a number of different types of leukocytes exist which include lymphocytes (both B and T cells, Natural Killer (or "NK") cells and various subsets thereof), monocytes and granulocytes (including neutrophils, eosinophils and basophils in all maturational stages). Because of the wide possible range of cell types and the range of maturational stages of any one cell type, obtaining whole blood counts and leukocyte differentials often is a difficult and complex procedure in the normal individual but it is more difficult and complex in an abnormal individual. This complexity is emphasized even more when the analysis of bone marrow samples is attempted.

Traditionally, whole blood counts (i.e., number of cells per standard unit of volume) and leukocyte differentials (i.e., number of cells of a given type per standard unit of volume) have been performed manually by counting a small volume of cells using a light microscope and then multiplying the number counted by a factor to account for the volume. Because of both the sample size measured and the level of skill required to distinguish among cell types, a high and often unacceptable degree of variability may be introduced by this method.

Recently, instrumentation has been devised to obtain whole blood counts or leukocyte differentials without having to resort to manual microscopic examination. Currently available instrumentation detect cells either electronically by aperture impedance (e.g., Coulter Counter ™, described in Coulter, Proc. Nat. Electronics Conf., 12:1034 (1956)) or optically by light scattering and absorption (e.g., Technicon H-6000 ™, described in Breakell et al., Blood Cells, 11:257 1985)). In these instruments, the red blood cell fraction must be separated from the leukocytes and each measurement is taken independently of the other. This must be done because RBC generally outnumber leukocytes by at least 1000:1 in the normal patient. In the abnormal patient (e.g., leukopenic patent), this ratio may be substantially higher.

Other means to obtain leukocyte differentials also exist. Flow cytometers, which are generally described in U.S. Pat. Nos. 4,661,913, 4,284,412 and 3,826,364, and in an article by Herzenberg et al., Sci. Am., 234:108 (1976), have been used to identify different populations of leukocytes in a heterogeneous sample by detecting multiple independent parameters on individual cells that pass through the sensing region. Typically, these parameters include forward light scatter (FLS which is a measure of relative particle size), orthogonal light scatter (OLS which is a measure of relative granularity) and fluorescence. Fluorescence may be measured from cells that incorporate a nucleic acid stain or may be measured from cells bearing surface markers which are labelled with monoclonal antibodies (MAbs) conjugated directly or indirectly to fluorochromes, as described, for example, in U.S. Pat. No. 4,520,110. Separate channels within the flow cytometer sense and record each of the various cell measurements. By combining and comparing these parameters, the various leukocyte components may be distinguished. U.S. Pat. No. 4,727,020 provides one example of how a flow cytometer may be used in this method to obtain leukocyte differentials from blood. This approach, however, is limited to leukocyte differentials and only those obtained from blood.

Taken together, there is no single, standard, accurate instrumentation or methodology currently available that allows a single sample of blood or bone marrow to be analyzed such that all the various cell types present in blood and bone marrow may be discriminated and then counted.

SUMMARY OF THE INVENTION

The present invention comprises a method for the simultaneous, multi-parameter analysis of cells in a body fluid, wherein the fluid comprises either spinal, peritoneal or brain fluid, urine or whole blood and additionally may comprise a tissue cell suspension, wherein the tissue comprises bone marrow aspirates, lymph node, spleen or liver cells such as from a biopsy, and wherein the parameters comprise at least two measures of light scatter for each cell examined and at least three measures of fluorescence emmission or activity from each cell examined. The method comprises the steps of taking a sample of fluid from an individual, combining the fluid sample with at least two dyes and with at least one labelled cell surface marker, wherein said dyes will independently assess different characteristics of the cells in the sample and wherein said marker recognizes an antigen that is differentially expressed in on cells of different lineages, to form a labelled solution. Each of the dyes and label is fluorescent and has a peak emission spectra that is distinguishable from the others. The labelled solution then is passed through a detection instrument, wherein each cell in the solution is examined substantially one at a time, and measurements of fluorescence intensity and light scatter are taken for each cell examined. The measurements (or parameters) taken for each cell may be stored in a data storage and analysis system and recombined and analyzed in real time or at a later time By analyzing these several parameters, the cell types and lineages that comprise blood and bone marrow samples may be distinguished and identified.

More specifically, the method comprises the steps of taking a body fluid sample from an individual, combining the fluid sample with nucleic acid dyes, such as an RNA dye, a DNA dye, and a labelled monoclonal antibody, which recognizes a cell surface antigen that is differentially expressed on different cell lineages, to form a labelled solution, passing the labelled solution through a flow cytometer, measuring fluorescence intensity, OLS and FLS and storing the data recorded for analyses. Each of the nucleic acid dyes and immunolabel is fluorescent, is excitable at the same wavelength and has a peak emission spectra that is distinguishable from the others.

A kit containing the nucleic acid dyes and labelled cell surface markers useful herein also is included within the scope of the present invention.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

All six figures represent log scale color dot plots containing approximately 22,000 cells from a fluid sample labelled with the nucleic acid dyes LDS-751 and Thiazole-Orange and with a fluroescently labelled CD45 MAb such as HLe-1(PE). labelled cells were analyzed on a FACScan TM flow cytometer equipped with a single argon laser tuned to 488 nm (Becton Dickinson Immunocytometry Systems (BDIS)), and measurements of OLS and FLS and fluorescence intensity were taken on each cell. Data acquisition of the five parameters digitized and stored in list-mode was performed using a Consort 30 computer (BDIS). Data analyses and printouts were performed using Paint-A-Gate TM software (BDIS).

DETAILED DESCRIPTION OF THE INVENTION

The present invention comprises a method for the simultaneous, multi-parameter analysis of cells in a body fluid, wherein the fluid comprises either spinal, peritoneal or brain fluid, urine or whole blood and may additionally comprise a tissue cell suspension, wherein said cell suspension is prepared from bone marrow aspirates, liver, spleen or lymph node, such as from a biopsy, and wherein the parameters comprise at least two measures of light scatter for each cell examined and at least three measures of fluorescence activity from each cell examined. The method comprises the steps of taking a sample of body fluid from an individual, combining the fluid sample with at least two dyes and with at least one labelled cell surface marker, wherein each of said dyes will independently assess different characteristics of the cells in the sample, and wherein said marker recognizes an antigen that is differentially expressed on cells of different lineages, to form a labelled solution. Each of the dyes and label is fluorescent and has a peak emission spectra that is distinguishable from the others. The labelled solution then is passed through a detection instrument, wherein each cell in the solution is examined substantially one at a time, and measurements of fluorescence intensity and light scatter are taken for each cell examined. The measurements (or parameters) taken for each cell may be stored in a data storage means and recombined and re-analyzed in real time or at a later time.

The present invention will allow for the discrimination and identification of cells in a fluid sample by the analyses of at least five parameters. Desirably, the method of the invention comprises the steps of: 1) isolating a cell containing fluid sample from an individual where, preferentially, the body fluid comprises either whole blood or bone marrow aspirates; 2) adding two fluorescent nucleic acid dyes to said sample to differentially label the DNA and RNA in each cell, wherein each dye has a fluorescent peak emission spectra different from the other; 3) adding a fluorescent labelled cell surface marker to said sample, wherein said marker recognizes an antigen that is differentially expressed on said cells in said fluid and wherein said fluorescent immuno-label has a peak emission spectra different from said fluorescent dyes; and 4) analyzing said cells in said sample in an automated instrument capable of detecting and recording both fluorescence of individual cells at or near said peak emission spectra and OLS and FLS of individual cells.

In the preferred embodiment, the detection instrument comprises a flow cytometer, such as a FACScan TM (BDIS) Preferably, the flow cytometer is equipped with a single laser for excitation of said fluorescent labelled cells such as an argon ion laser and is tuned at or near 488 nm. The fluorescent nucleic acid dyes and fluorescent label, therefore, must be excitable at 488 nm. Preferably, LDS-751 (Exciton) is used as a DNA dye and Thiazole-Orange (BDIS) is used as an RNA dye. LDS-751 has a peak emission spectra at 670 nm, and Thiazole-Orange has a peak emission spectra at 530 nm. Other fluorescent nucleic acid dyes that may be suitable for practice in this invention include those described in U.S. Pat. No. 4,544,546.

It will be appreciated by those skilled in the art that if the flow cytometer is equipped with more than one laser, the fluorescent dyes and/or fluorescent label may be excited at different wavelengths. In such an embodiment, the only requirement is that the peak emission spectra for the dyes and immunofluorescent label all differ. Flow cytometers equipped with helium/neon and argon ion lasers tuned to 633 nm and 488 nm respectively include FACStar Plus TM (BDIS).

Also in the preferred embodiment, the cell surface marker is a monoclonal antibody that will selectively attach to a cell surface antigen that is differently expressed on the surface of hematopoietic cells. Desirably, the antigen will be expressed in different amounts on the various types and maturational stages of nucleated cells. One such antigen is CD45. This antigen has a molecular weight of approximately 180-220kD and is expressed in different levels on all lymphocytes, monocytes and granulocytes but is absent from mature platelets or RBC. Monoclonal antibodies that react specifically with the CD45 antigen (i.e., CD45 MAbs) include HLe-1 (also referred to an Anti-Leukocyte, BDIS) and LCA (Dako Corp.). Preferably, HLe-1 is used.

The CD45 MAb is tagged directly with a fluorescent label such as a fluorochrome. In the direct method, the MAb is conjugated directly to a fluorescent label by means known to those skilled in the art. U.S. Pat. No. 4,520,110 provides one method for conjugating a fluorescent label to a MAb.

In the preferred embodiment, the fluorochrome is a phycobiliprotein, such as phycoerythrin (PE), which can be excited at 488 nm and has an emission peak at 575 nm. The combination of HLe-1 and PE is generally referred to as HLe-1(PE).

Other fluorochromes also may be used in this invention. The only requirements are that the fluorochromes excite at 488 nm, if an argon laser is used, or at some other wavelength, if a dual laser source is used (e.g., 633 nm for a He/Ne laser), and that the fluorochrome have a peak emission spectra that does not overlap with the nucleic acid dyes.

Further, it is desirable to have the flow cytometer coupled to means to record and analyze the data collected on each individual cell. Means to record and analyze the data may include a personal computer equipped with appropriate software. The software should be capable of analyzing at least five parameters for each cell, of discriminating between or identifying populations of like cells in five-dimensional space and of displaying at least two of the parameters in two dimensions. In addition, the software should be capable of gating on one or more parameters and displaying combination of the other parameters in two dimensions.

In the preferred embodiment, Paint-A-Gate TM software (BDIS) is used in connection with a Consort 30 data storage and analysis system (BDIS). The software is fully described in U.S. Serial No. 046,619 (filed May 7, 1987 and which issued as U.S. Pat. No. 4,845,653) which is commonly assigned to the assignee hereof.

In addition to the method described herein, the present invention also comprises a kit for multi-parameter analysis of cells in a body fluid. The kit may comprise a first container containing at least two nucleic acid dyes to label the DNA and RNA in each cell, wherein the dyes have peak emission spectra that are distinguishable from the others, and a second container containing a fluorescently labelled cell surface marker, wherein the cell surface marker will specifically react with a cell surface antigen that is differentially expressed on the different cells that comprise the sample. Desirably, the dyes are nucleic acid dyes which will differentially label DNA and RNA. In the preferred embodiment, the nucleic acid dyes are LDS-751 and Thiazole-Orange, and the fluorescently labelled cell surface marker is HLe-1(PE). It will be appreciated by those skilled in that art that other of the nucleic acid dye and/or cell surface marker combinations disclosed herein may comprise the kit. Similarly, it will be appreciated that the nucleic acid dyes and/or cell surface markers may be separately contained in the containers.

EXAMPLES

Peripheral blood from normal volunteers was collected by venipuncture into Vacutainer TM brand evacuated blood collection tubes containing EDTA($k_3$) as anticoagulant (Becton Dickinson). Blood also was collected from a patient with B Cell Chronic Lymphocytic Leukemia (B-CLL) graded stage IV according to RAI. Blood cell counts determined on an automated blood cell analyzer (Hl, Technicon were: RBC $3.3 \times 10^9$/ml; leukocytes $81.9 \times 10^6$/ml; and platelets $35 \times 10^6$/ml corrected after manual counting to $20 \times 10^6$/ml. Bone marrow aspirates were obtained from normal volunteers. The aspirates were transferred into Vacutainer TM brand evacuated blood collection tubes and diluted 1:1 with RPMI 1640 (GIBCO).

For each test, 10 ul of a blood or bone marrow sample was used. The samples were incubated for 30 minutes with 10 ul of a LDS-751 solution (0.1 mg in 5 ml PBS), 10 ul of a Thiazole-Orange solution (0.1 mg in 1 ml PBS) and 10 ul of HLe-1(PE). The sample was diluted with 1 ml phosphate buffered saline (PBS) before measurement.

Spectral compensation was used to correct for PE emission entering the LDS-751 channel (5% subtraction), LDS-751 entering the PE channel (11% subtraction), PE entering the Thiazole-Orange channel (23% subtraction) and Thiazole-Orange entering the PE channel (0.4% subtraction). No compensation was required between Thiazole-Orange and LDS-751 channels.

Flow cytometric measurements were performed on a FACScan TM flow cytometer equipped with a single argon ion laser. Data acquisition of the five parameters digitized and stored in list-mode was performed with the FACScan TM research software using a Consort 30 TM computer. For each sample, 22,000 cells were analyzed. For discrimination within the nucleated cells, the acquisition was performed while gating on the fluorescence intensity of LDS-751 and Thiazole-Orange. Data analysis was performed using the Paint-A-Gate TM software program which allows visualization of multi-parameter data.

It will be appreciated by those skilled in the art that analysis of a sample may be performed in two separate procedures. Initially, a split-sample of body fluid is taken, one or more of which is diluted as above and one of which is not diluted or is diluted less. Then, the above described method is followed using one split-sample to identify and discriminate RBC, platelets and reticulocytes while gating on but not counting nucleated cells. The method also is followed for identifying and discriminating the nucleated cells while gating on but not counting the non nucleated cells. Splitting the sample and examining the nucleated cells in less diluted format will allow the relatively rarer nucleated cells in the sample to be counted in a more rapid fashion.

Cell sorting was performed on a FACS 440 TM which was adapted to detect two light scatter signals and three fluorescence signals using a single argon ion laser tuned to 488 nm. The cells were sorted into RPMI 1640 containing 10% fetal calf serum (FCS). The sorted cells were centrifuged for 5 minutes at 200 g and resuspended in 100 ul RPMI containing 10% FCS. Microscope slide preparations were made using a Shandon Cytocentrifuge (Southern Product Ltd., England). The slides were stained with Wright Stain and examined with a light microscope. For reticulocyte identification, 100 ul of a 1% new Methylene blue solution was added to the resuspended sorted cells. The cells were transferred to a slide, covered and examined with a light microscope.

Analyses of the five parameter list-mode files were performed with a computer program which utilized color to identify clusters of dots in multiple dimensions. Different combinations of the five parameters were displayed at one time. Clusters of cells identified by one combination of parameters were painted a color which then appeared simultaneously in the other projections of the data.

Figure 1:
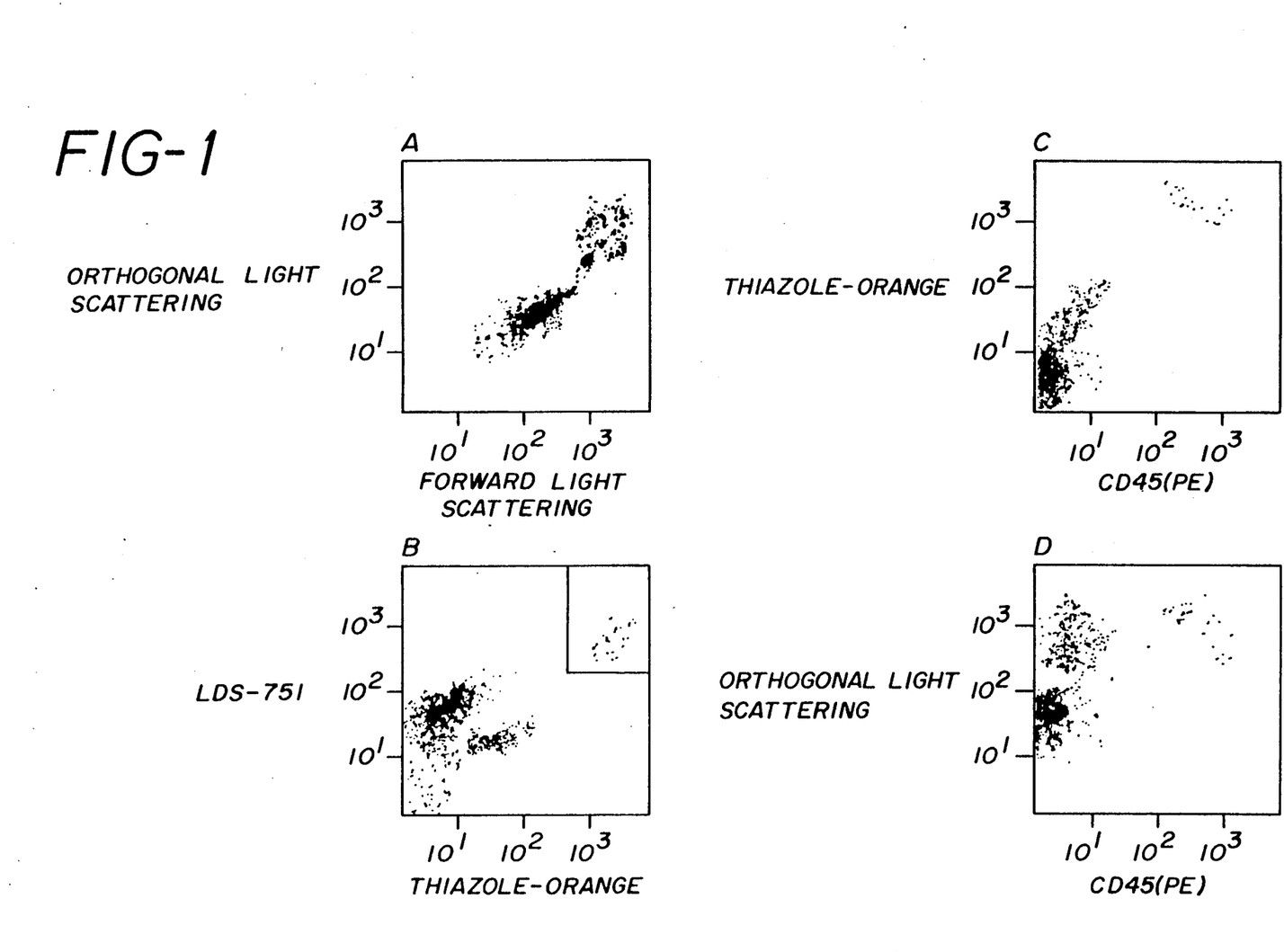
FIG. 1 comprises several dot plots of cells from a normal peripheral blood sample analyzed by various combinations of the five parameters, wherein cells colored yellow are erythrocytes, cells colored black are leukocytes, cells colored red are reticulocytes and particles colored dark blue are platelets.

A large range of light scatter signals is obtained from unlysed blood samples as a result of the presence of small platelets (1–4u), erythrocytes (6–8u) and larger leukocytes (6–20u). In order to assess the whole range of light scattering signals, the forward and orthogonal light scattering signals were acquired using four decade logarithmic amplifiers. Under these conditions two major populations of cells were identified in whole blood. See FIG. 1a. Further discrimination between the cell populations required additional parameters.

Thiazole-Orange has a higher affinity or preference towards RNA as compared with DNA and undergoes fluorescence enhancement upon binding. The peak emission of the bound dye occurs at 530 nm. In contrast, LDS-751 has a higher affinity or preference for DNA as compared with RNA. This dye also undergoes fluorescence enhancement upon binding, but with maximal emission at 670 nm. Although, it is recognized that platelets do not have a nucleus, LDS-751 will selectively stain such cells. Thus, it is expected that dyes other than LDS-751 also will selectively bind to platelets and other nucleated cells to distinguish platelets from the non nucleated RBC.

Thiazole-Orange and LDS-751 in combination provide large separation between erythrocytes, which lack both RNA and DNA, and nucleated leukocytes which have both nucleic acids. In FIG. 1b, the erythroyctes and the leukocytes, (black, in the upper right hand corner) are separated by almost three orders of magnitude in their fluorescence signals. No significant interference between these dyes was observed for nucleated cells.

Although Thiazole-Orange and LDS-751 could be used to distinguish between erythrocytes, reticulocytes and platelets, there was an interaction between these dyes observed in both the platelets and reticulocytes. For platelets, the order in which both dyes were added did affect fluorescence intensity. Addition of LDS-751 before or together with Thiazole-Orange inhibited the staining of the platelets with Thiazole-Orange. Platelets were stained with Thiazole-Orange only when the dye was added alone or if it preceded the addition of LDS-751. Among the reticulocytes, the fluorescence intensity with Thiazole-Orange was slightly less in the presence of LDS-751. By incubating the samples simultaneously with Thiazole-Orange and LDS-751, maximal separation between platelets and reticulocytes was obtained while maintaining good separation of these populations with respect to the erythrocytes.

The separation of emission spectra between Thiazole-Orange and LDS-751 permitted the binding of a MAb conjugated with PE to be assessed simultaneously. CD45 was selected since the antigen recognized by this antibody has been shown to occur in different densities on cells of different lineages. Combining the immunofluorescence intensity with the forward and orthogonal light scattering allowed an extensive differential analysis of nucleated cells as described in the following sections.

I. Differential Analysis of Normal Blood Cells

Peripheral blood was incubated with LDS-751, Thiazole-Orange and HLe-1(PE). The blood preparation was diluted 1:100 with PBS before measurement.

In view of the complexity of the data, the identification of the different blood cell populations is described separately. The identity of the cell subpopulations referred to were verified by microscopic examination of the sorted cells. The purity of the sorted cell fractions was greater than 90%, with the majority of contaminating cells being erythrocytes. The high frequency of the erythrocytes allowed them to be deflected together with the gated cell population as a result of the setting of the threshold during the sorting of the leukocyte populations.

The predominant cell population in blood is composed of mature erythrocytes (RBC). RBC were identified by their relatively large forward and orthogonal light scatter signal (FIG. 1a, yellow), lack of fluorescence with LDS-751 and Thiazole-Orange (FIG. 1b) and absence of anti-CD45 binding (FIG. 1c,d).

The reticulocytes (red in FIG. 1) were distinguished from the mature erythrocytes primarily by their reactivity with Thiazole-Orange (FIG. 1b). The reticulocytes have a slightly enhanced fluorescence intensity with LDS-751 as compared with erythrocytes. Neither RBC nor reticulocytes express surface antigens recognized by CD45 (FIG. 1c,d). The reticulocytes could not be distinguished from leukocytes and RBC based on their light scatter characteristics (FIG. 1a).

Nucleated red cells, not normally found in peripheral blood, are discussed later as part of the analysis of bone marrow.

Platelets were characterized by their relative low forward and orthogonal light scatter (FIG. 1a, blue) as well as their staining for LDS-751 (FIG. 1b). The platelets were clearly separated from the RBC (yellow), reticulocytes (red) and leukocytes (black) (FIG. 1b) using these three parameters. As with the erythroid cells, the platelets did not express the antigens recognized by CD45 (FIG. 1c,d). Using multi-parameter analysis, "normal" platelets can be characterized as particles with relatively low light scatter signals, a larger fluorescence intensity with LDS-751 than that of RBC, no reactivity with Thiazole-Orange, and an absence of CD45 binding.

Leukocytes were characterized by a relatively large orthogonal and forward light scattering signal (FIG. 1a, black). Although their light scatter characteristics were similar, the leukocytes were clearly separated from the erythroid cells (yellow) by their large fluorescence signals generated by both LDS-751 and Thiazole-Orange (FIG. 1b). This resolution provides an accurate means of counting white blood cells in the presence of an overwhelming number of RBC. A further distinction of leukocytes from platelets, RBC and reticulocytes was obtained by their reactivity with CD45 (FIG. 1c,d).

Figure 2:
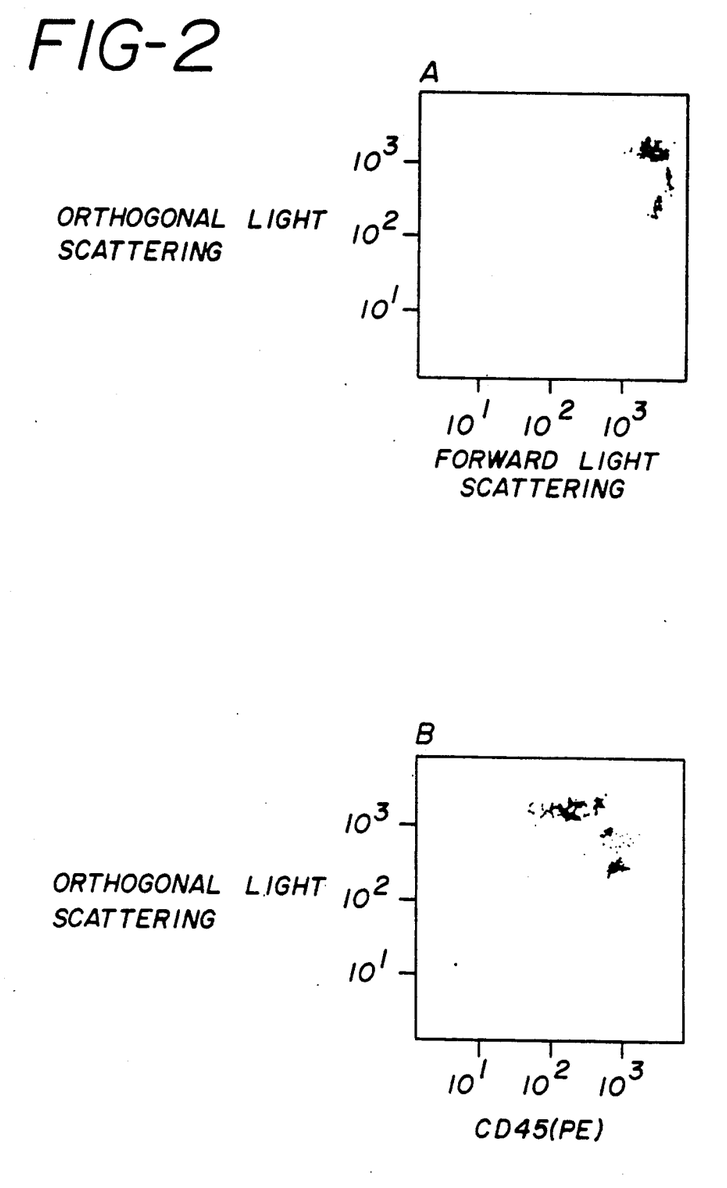
FIG. 2 comprises several dot plots only of the nucleated cells of the blood sample analyzed in FIG. 1 and gated on LDS-751 and Thiazole Orange fluorescence (FIG. 1b), wherein cells colored dark blue are lymphocytes, cells colored red are monocytes, cells colored green are neutrophils and cells colored black are eosinophils.

In order to analyze the nucleated cells in more detail, a gate was set on Thiazole-Orange and LDS-751 as indicated in FIG. 1b. A leukocyte differential was obtained by correlating the light scatter properties of the nucleated cells with the fluorescence intensity of CD45. See FIG. 2a. Lymphocytes (blue) were characterized by the brightest expression of CD45 antigen and the lowest orthogonal light scatter signals. Monocytes (red)

were identified as binding slightly less CD45 than lymphocytes but showing a larger forward and orthogonal light scatter signal. Neutrophilic granulocytes (green) dimly expressed CD45 antigen and had large light scattering signals. Eosinophilic granulocytes (black) bound the same amount of CD45 as monocytes but were distinguishable from these cells by larger orthogonal light scatter signal and lower forward light scattering signal.

II. Differential Analysis of Normal Bone Marrow Cells

Figure 3:
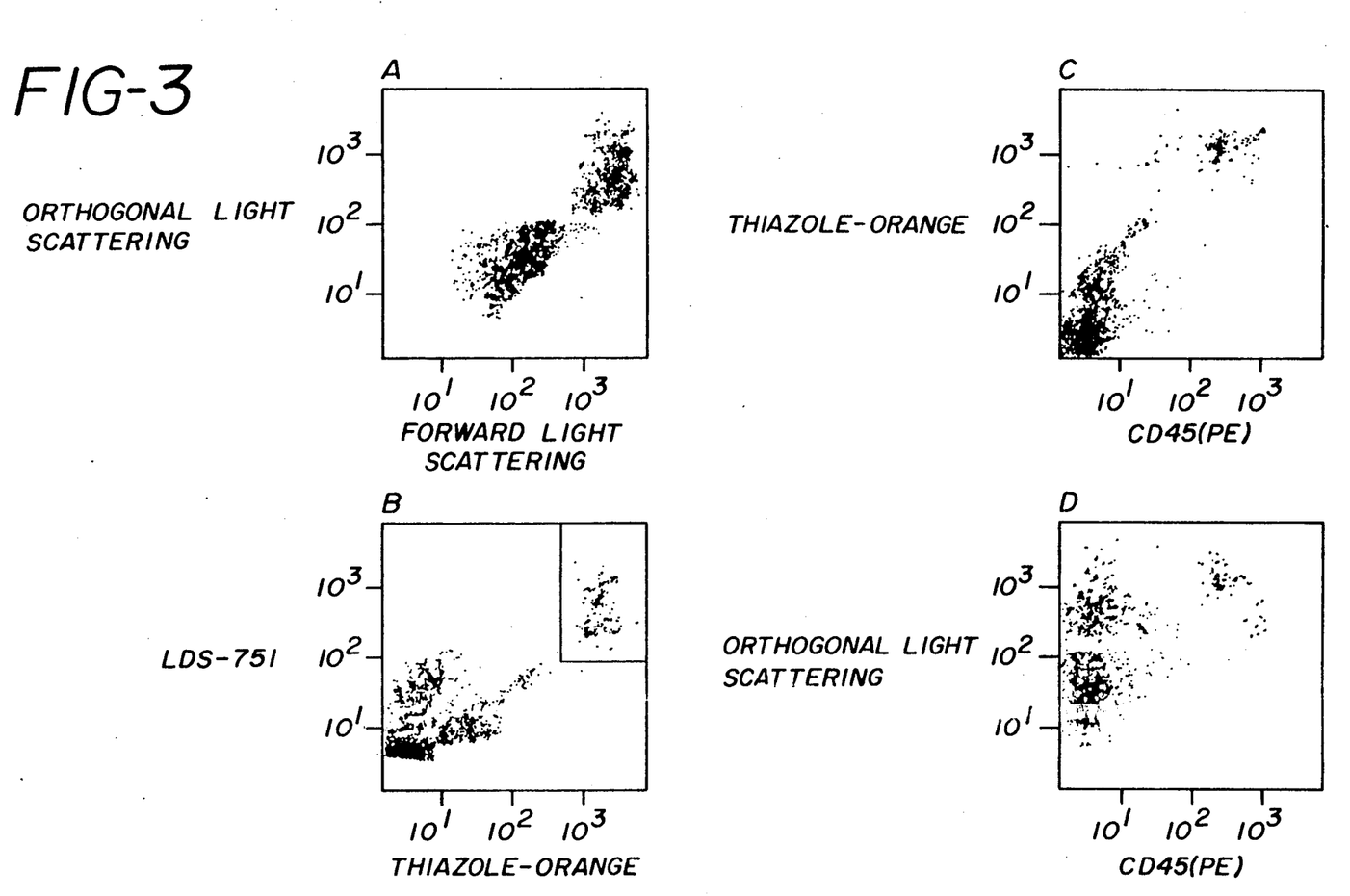
FIG. 3 comprises several dot plots of cells from a normal bone marrow aspirate analyzed by various combinations of the five parameters, wherein the cell types are colored as in FIG. 1.

The five dimensional analysis used on blood also was applied to the quantitative characterization of bone marrow. Aspirated bone marrow was incubated with LDS 751, Thiazole-Orange and HLe-1(PE) as was used for the peripheral blood. The acquisition of the data was performed with the same instrument settings that were used for analysis of peripheral blood. A typical experiment (using the same displays and color selection as was used in the analysis of peripheral blood) is shown in FIG. 3. The RBC (yellow), reticulocytes (red), platelets (dark blue) and nucleated cells (black) occupy similar locations in five dimensional space as do their peripheral blood cells counterparts (compare FIGS. 1 and 3).

There are interesting differences between the blood end marrow populations. In the analysis of the platelets, the light scatter region typical for these cellular particles was painted blue in FIG. 3 as it was in the analysis of the blood sample (FIG. 1). In contrast with peripheral blood, a majority of these events from bone marrow did not stain with LDS-751 (identified as black dots projected on yellow in FIG. 3b), therefore, these events were not identified as normal platelets. Cell sorting of this population showed mainly debris, including bone marrow spicules and cellular particles which has not been identified.

Figure 4:
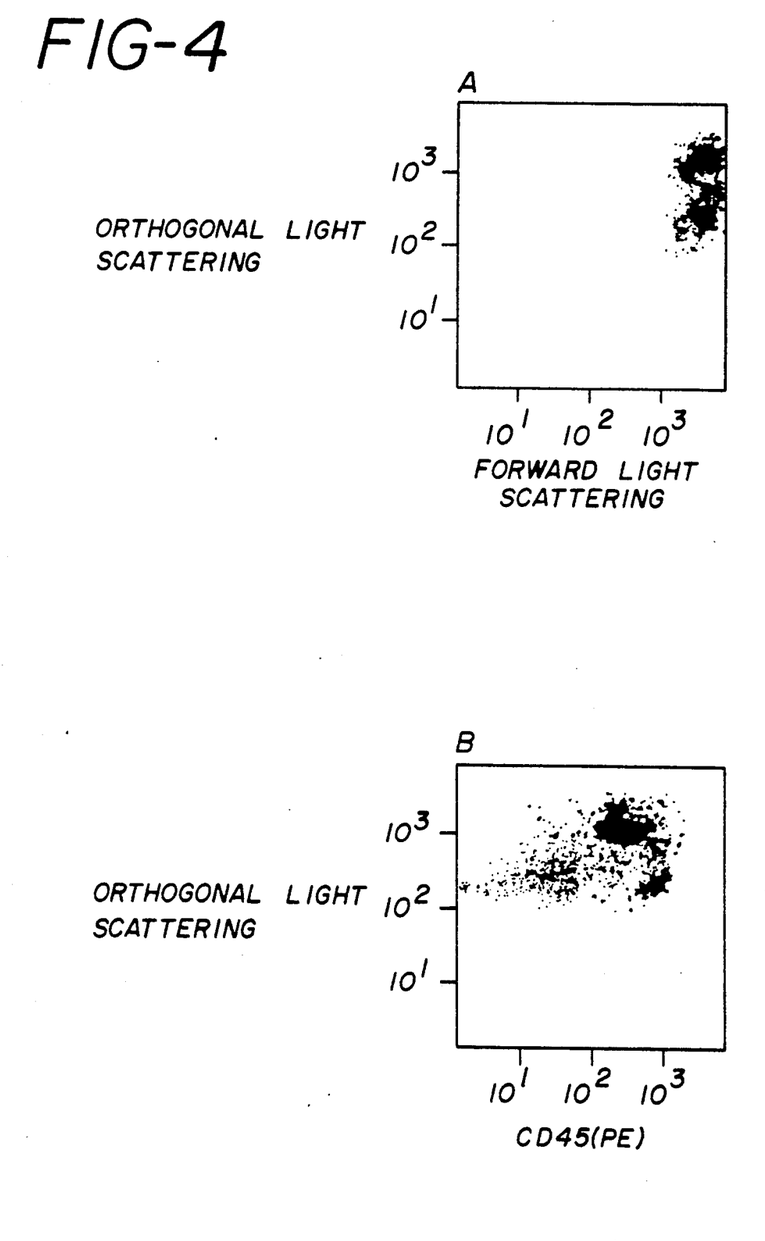
FIG. 4 comprises several dot plots only of the nucleated cells from the bone marrow sample analyzed in FIG. 3 and gated on LDS-751 and Thiazole-Orange fluorescence, wherein the cell types are colored as in FIG. 2 and wherein nucleated erythroid cells are colored purple and immature leukocytes (blast cells) are colored light blue.

The nucleated bone marrow cells were identified by their large fluorescence signals with LDS-751 as well as Thiazole-Orange (FIG. 3b). A gate was set on LDS-751 and Thiazole-Orange intensity, as indicated in FIG. 3b, to collect more nucleated cell events. The light scattering properties and their correlation with the immunofluorescence signals with CD45 of these nucleated cells is shown in FIG. 4. The typical locations of lymphocytes, monocytes and granulocytes as identified from studies of peripheral blood were colored dark blue, red and green respectively.

For three different bone marrow aspirates, differential morphological counts were made of the nucleated cells sorted by orthogonal light scatter and CD45 expression. The regions sorted were those indicated by the different colors in FIG. 4b. The results were present in Table I as average percentage of the nucleated cells found in the three experiments.

TABLE I

Differential Morphological Counts of Normal Nucleated Human Bone Marrow Cells Sorted by Orthogonal Lightscattering and CD45 Expression +.

| | Lymphocytic | Monocytic | Granulocytic | Erythroid | Undifferentiated Blast |
|---|---|---|---|---|---|
| dark blue | 98 | 1 | 0 | 1 | 0 |
| red | 5 | 79 | 16 | 0 | 0 |
| green | 0 | 7 | 91 | 2 | 0 |
| purple | 0 | 0 | 0 | 100 | 0 |
| light blue | 56* | 3* | 30* | 3* | 8 |

The colors refer to the regions illustrated in FIG. 4B. The data are given as percentage of nucleated cells.
+ n = 3
*blast Light microscopic examination of the sorted populations confirmed the lineage classification of these cells, however, not all of the cells in the dark blue, red and green region were mature. Within the population colored green, in addition to mature neutrophils, bands and metamyelocytes were also found. Approximately 5% of the cells colored dark blue (lymphocytes) were lymphoblast and 20% of the cells colored red (monocytes were immature monomyeloid cells).

In contrast with peripheral blood, two populations of bone marrow cells were identified having low orthogonal light scatter signals and dimly expressing (CD45 antigen, colored purple and light blue respectively in FIG. 4b. From this figure it is obvious that there is no clear separation between the population of cells colored light blue and the other painted populations. Light microscopic examination of the population of cells which expressed the lowest level of CD45 antigen (purple), revealed that it consisted exclusively of normoblasts and erythroblasts (Table I). The population expressing slightly higher amounts of CD45 antigen (light blue) contained the most immature cells including monomyeloid and lymphoid precursors and a few erythroblasts (Table I).

III. Differential Blood Cell Analysis In A Thrombocytopenic B-Chronic Lymphocytic Leukemic Patient The utility of this technique is demonstrated in the analysis of blood from a B-CLL patient. A stage IV of RAI B-CLL patient was chosen because abnormal counts are commonly found for all blood cell lineages. The 10 to 100 fold increase in the number of lymphocytes makes the distinction of these cells from residual normal leukocytes and reticulocytes more difficult. Furthermore, the low platelet counts in these patients makes platelet enumeration less reliable.

The blood from the B-CLL patient was incubated with LDS-751, Thiazole-Orange and HLe-1(PE) as was done for normal blood. The data are displayed in the same manner as was chosen for normal peripheral blood (FIG. 1) and bone marrow (FIG. 3): RBC were painted yellow; reticulocytes appeared red; platelets were blue and nucleated cells were black colored (FIG. 5a,b,c,d).

Figure 5:
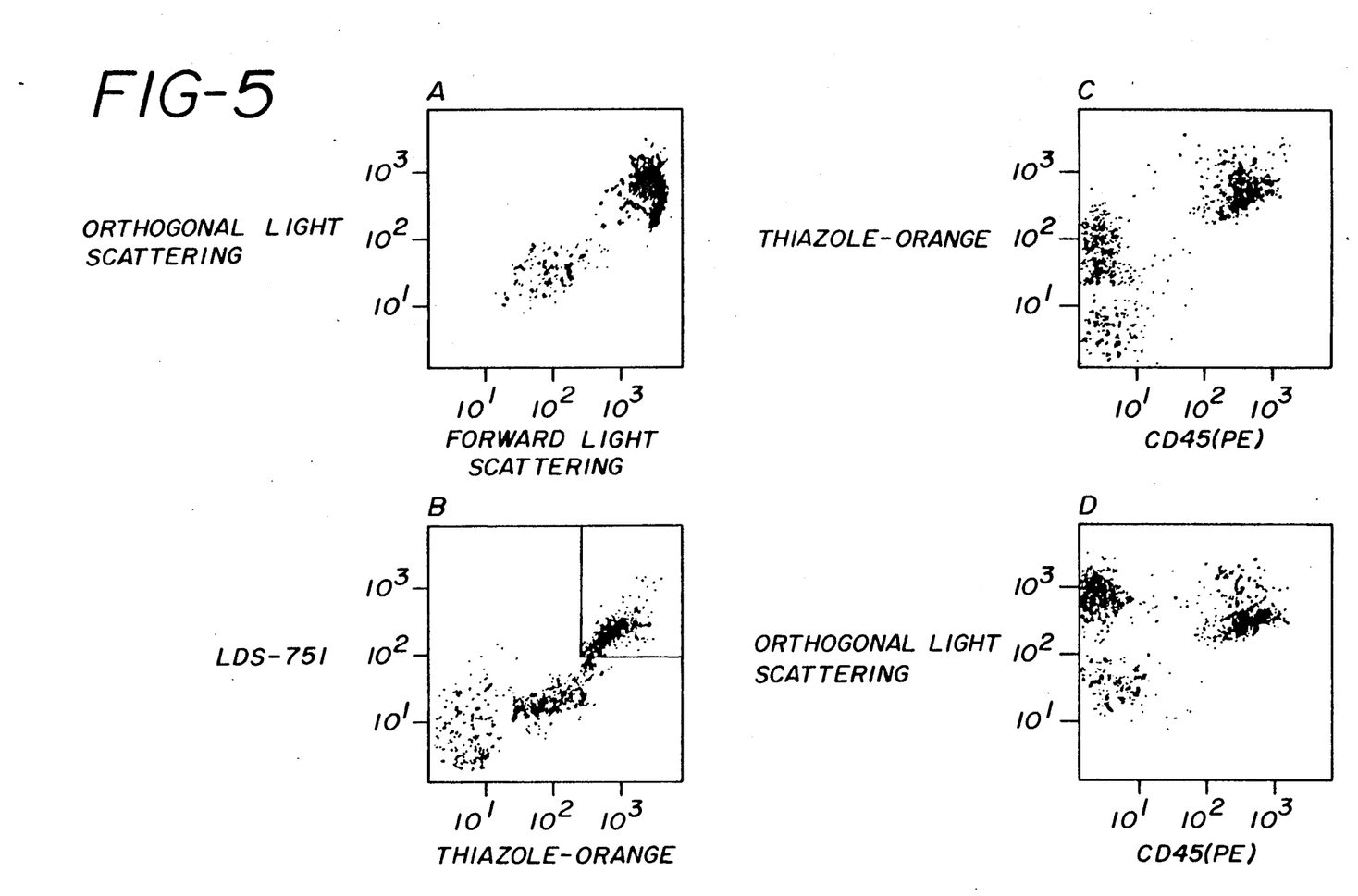
FIG. 5 comprises several dot plots of peripheral blood cells from a thrombocytopenic B-CLL patient analyzed by various combinations of the five parameters wherein the cells are colored as in FIG. 1.

The frequency of cells occurring in the light scatter region typical for platelets (FIG. 5a) was low compared with normal peripheral blood (compare blue dots in FIG. 1a,b with FIG. 5a,b). Only a few of the dots identified as platelets with light scattering in FIG. 5a (blue) show the fluorescence intensity with LDS-751 typical for platelets in FIG. 5b and can be considered as normal platelets. The discrimination of platelets from reticulocytes (red) is still excellent FIG. 5b).

As a consequence of the large increase in frequency of nucleated cells (black), the separation of the leukocytes and reticulocytes (red) obtained with LDS-751 and Thiazole-Orange is less clear. However, the leukocytes can be clearly separated from the reticulocytes based on their expression of the CD45 antigen (FIG. 5c,d).

Figure 6:
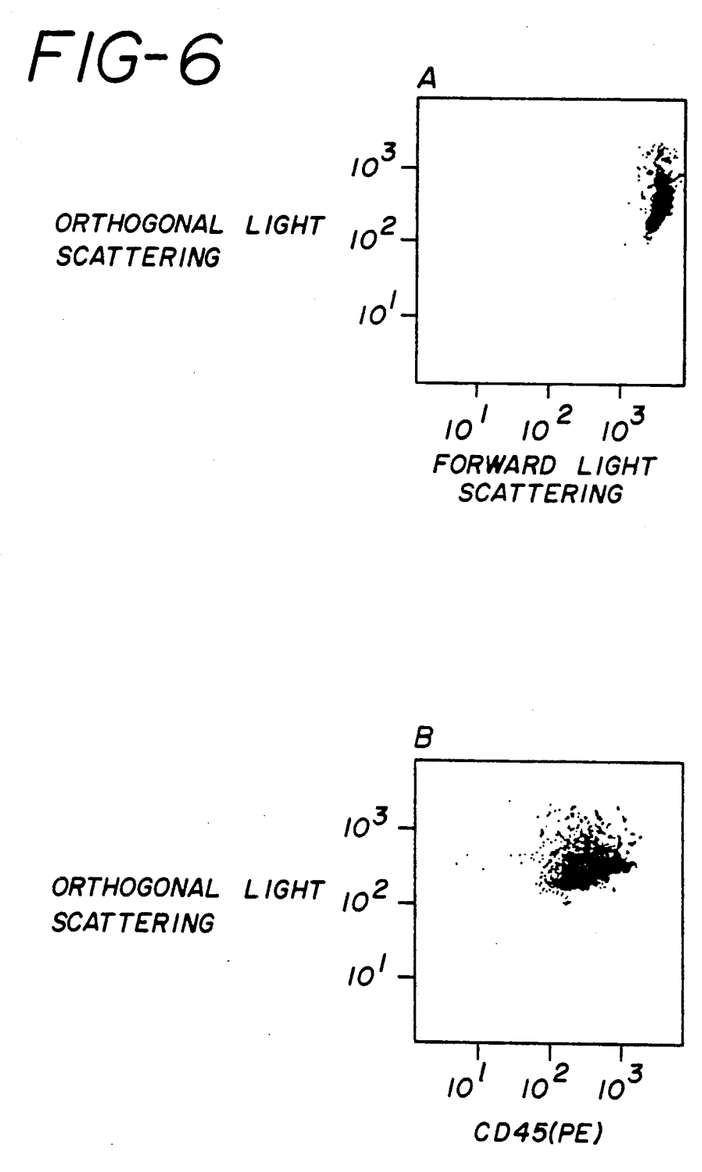
FIG. 6 comprises several dot plots only of the nucleated cells from the blood sample analyzed in FIG. 5 and gated on LDS-751 and Thiazole-Orange fluorescence wherein the cells are colored as in FIG. 4.

The light scatter properties and CD45 antigen expression of the nucleated cells (gated in FIG. 5b) is shown in FIG. 6a,b. The majority of cells dimly express CD45 antigen and exhibit low forward and orthogonal light scatter signals (light blue) characteristics of immature lymphocytes. Only a few leukocytes were detected as normal, lymphocytes (dark blue), granulocytes (green) and monocytes (red), although the separation was not distinct as a result of the overwhelming number of immature lymphoid cells. Note the few cells (purple) which did not express CD45 antigen and which had a low orthogonal light scattering signal See FIG. 6B. These cells were identified as nucleated erythroid cells consistent with the large increase in reticulocytes in this patient.

IV. Whole Blood as a Bone Marrow Contaminant

Often during the removal of bone marrow aspirate, blood may be introduced into the aspirate as a contaminant to the sample. Thus, if one were to analyze the sample without correction for the blood contaminants, the leukocyte differentials could be in error.

By running a blood sample as described in Example I above, the percentages of white blood cell types in the blood may be calculated. Once the marrow sample is run as described in Example II, the expected percentages of white blood cells in the blood sample may be subtracted from the bone marrow sample to give a more accurate reading free from blood contaminants (assuming that in fact all the contaminants are blood derived).

Thus, for example, lymphocytes, granulocytes and monocytes comprise 1.0, 1.0 and 0.2 percent of total cells in a blood sample respectively, with the remaining 97.8% of the cells being essentially RBC. As a result, there are approximately one lymphocyte and granulocyte and 0.2 monocytes per 100 RBC in the blood sample. The absolute counts of the same cells in a bone marrow sample is 800, 490 and 165 respectively in a 20,000 cell sample with the remainder of the cells being essentially RBC (i.e., 18,545). Thus, for the purpose of example only, the number of lymphocytes, granulocytes and monocytes expected to be contaminating the bone marrow sample would be 185 lymphocytes (i.e., 1% × 18,545), 185 granulocytes (i.e., 1% × 18,545) and 37 monocytes (i.e., 0.2% × 18,545). The corrected counts, therefore, would be 615 lymphocytes, 305 granulocytes and 128 monocytes. By this method, more accurate counts may be obtained.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

It will be apparent to one of ordinary skill in the art that many changes and modifications can be made in the invention without departing from the spirit or scope of the appended claims.

What is claimed:

1. A method for multi-parameter analysis of cells in a body fluid wherein said method comprises the steps of:
   1) taking a fluid sample from an individual;
   2) adding two fluorescent nucleic acid dyes to said sample wherein one dye will differentially label DNA and wherein the other dye will differentially label RNA, and further wherein each dye has a fluorescent peak emission spectra different from the other;
   3) adding a fluorescently labelled cell surface marker to said sample, wherein said marker recognizes an antigen that is differentially expressed on said cells in said fluid sample and wherein said fluorescent label has a peak emission spectra different from said fluorescent dyes; and
   4) analyzing said cells in said sample in an instrument capable of detecting and recording three channels of fluorescence and two channels of light scattering for each of the cells in said sample.

2. The method of claim 1 wherein the body fluid comprises peritoneal, spinal or brain fluid, urine, whole blood or a cell suspension of bone marrow, lymph node, liver or spleen.

3. The method of claim 2 wherein the body fluid is whole blood.

4. The method of claim 2 wherein the body fluid is bone marrow.

5. The method of claim 1 wherein one of the nucleic acid dyes is LDS-751.

6. The method of claim 1 wherein one of the nucleic acid dyes is Thiazole-Orange.

7. The method of claim 1 wherein the two nucleic acids dyes are LDS-751 and Thiazole-Orange.

8. The method of claim 1 wherein the cell surface marker is a monoclonal antibody conjugated to a fluorochrome.

9. The method of claim 8 wherein the monoclonal antibody is a CD45 monoclonal antibody.

10. The method of claim 9 wherein the CD45 monoclonal antibody is HLe-1.

11. The method of claim 8 wherein the fluorochrome is phycoerythrin.

12. The method of claim 8 wherein the monoclonal antibody conjugated to a fluorochrome is HLe-1 conjugated to phycoerythrin.

13. The method of claim 1 wherein the sample taken in step 1) is split into one or more components and one of said components is diluted less than the other components.

14. A method for correcting a multi-parameter analysis of a bone marrow sample to adjust for increased white blood cell levels due to blood contamination of the bone marrow sample which comprises the steps of:
   1) performing the steps of the method of claim 1 on whole blood;
   2) determining the percentages of various white blood cell components in the blood;
   3) performing the steps of the method of claim 1 on bone marrow;
   4) determining the absolute counts of various white blood cell components in the bone marrow; and
   5) multiplying each of the percentage obtained in step (2) by the total number of cells in the bone marrow sample and subtracting that number from the respective absolute counts obtained in step 4).

15. A method for five-parameter analysis of cells in a blood sample wherein said method comprises the steps of:
   1) taking a blood sample from an individual;

2) adding LDS-751 and Thiazole-Orange to said sample;
3) adding a CD45 monoclonal antibody conjugated to phycoerythrin to said sample;
4) passing said sample through a flow cytometer having single laser source tuned to 488 nm and capable of recording and storing measurements of orthogonal and forward light scatter and of LDS-751, Thiazole-Orange and phycoerythrin fluorescence emissions for each cell in said sample.

16. A method for five-parameter analysis of cells in a bone marrow sample wherein said method comprises the steps of:
1) taking a bone marrow sample from an individual;
2) adding LDS-751 and Thiazole-Orange to said sample;
3) adding a CD45 monoclonal antibody conjugated to phycoerythrin to said sample;
4) passing said sample through a flow cytometer having single laser source tuned to 488 nm and capable of recording and storing measurements of orthogonal and forward light scatter and of LDS-751, Thiazole-Orange and phycoerythrin fluorescence emissions for each cell in said sample.

* * * * *